(12) United States Patent
Nickel et al.

(10) Patent No.: US 6,528,659 B1
(45) Date of Patent: Mar. 4, 2003

(54) N-PROTECTED SYNTHESIS METHOD FOR USE IN MAKING PORPHYRINS

(75) Inventors: Eric G. Nickel, Atlanta, GA (US); Lanny S. Liebeskind, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/524,621

(22) Filed: Mar. 13, 2000

Related U.S. Application Data

(60) Provisional application No. 60/123,962, filed on Mar. 12, 1999.

(51) Int. Cl.[7] .................................................. C07D 207/30
(52) U.S. Cl. ........................ 548/524; 548/518; 548/527
(58) Field of Search ........................ 540/145; 548/518, 548/524, 527

(56) References Cited

U.S. PATENT DOCUMENTS

| | | | |
|---|---|---|---|
| 5,124,449 A | 6/1992 | Franck et al. | 540/472 |
| 5,241,062 A | 8/1993 | Wijesekera et al. | 540/145 |
| 5,554,764 A | 9/1996 | Verkade et al. | 548/455 |
| 5,672,717 A | 9/1997 | Verkade et al. | 548/518 |
| 5,756,724 A | 5/1998 | Vogel et al. | 540/145 |
| 5,760,217 A | 6/1998 | Wijesekera et al. | 540/145 |
| 5,767,272 A | 6/1998 | Wijesekera et al. | 540/145 |

FOREIGN PATENT DOCUMENTS

| | | |
|---|---|---|
| JP | 63238078 | 4/1988 |
| JP | 63238057 | 10/1988 |
| JP | 1238585 | 9/1989 |

OTHER PUBLICATIONS

Jerry March, Advanced Organic Chemistry, Fourth Ed., John Wiley & Sons, New York, pp. 352–354 and 421 (1992).*

Tietze et al, Synthesis, 1996 (7) 851–857 CAS Abstract Only.*

Abell, et al,. "*Synthesis and Properties of Ring–Deactivated Deuterated (Hydroxymethyl)pyrroles,*" J. Am. Chem. Soc., 120, 1741–1746 (1998).

Wang, et al., "*A General Synthesis of β–Aryl and Heterorarylpyyroles by Palladium–catalyzed Coupling Reaction of β–Tributylstannylpyrrole with Aryl and Heteroaryl Halides,*" Tetrahedron Letters, 37 (19) 3247–3250 (1996).

Kuroda, et al., "*A New Route For Meso–Substituted Prophyrin*", Tetrahedron Letters, 30 (18), 2411–2412 (1989).

Kinoshita, et al., "*Synthesis of 2–(Substituted Methyl)–3, 4–Disubstituted Pyrroles and Their Conversion into the Corresponding Porphyrins*" Bull. Chem. Soc. Jpn. 65,2660–2067 (1992).

Kinoshita, et al., *An Improved Method for the Preparation of Symmetrically Substituted Porphyrins via 2–Methoxymethyl–3,4–Disubstituted Pyrrole Derivatives*, Chem. Ltrs. 1107–1108 (1989).

Tietze, et al., "*Synthesis of N–Protected 2–Hydroxymethylpyrroles and Transformation into Acyclic Oligomers,*" Synthesis, 851–857 (1996).

Isaeva, et al., "Synthesis of Unsymmetrical Porphyrins From 5,5'–Substituted," Biorg Khim, 5 (7) 1146–1150 (1979).

Treibs et al., "*Über die Synthese und die Elektronenspektren ms–Substituierter Porphine,*" Liebigs Ann. Chem. 718, 183–207 (1968).

Lin, et al., "*Oxidative Cyclization of a,c–Biladienes: the Role of the Metal Ion,*" J. Porphyrin Phthalocyanines 2, 363–368 (1998).

Smith, et al., "*Synthesis and Preparation of Porphyin Compounds,*" Porphyrins and Metalloporphyrins,, Chap. 2, 29–58 (1975).

Manka, et al., "*High Yield Synthesis of 5,15–Diarylporphyrins,*" Tetrahedron Letters 30 (50), 6989–6992 (1989).

Taniguchi, et al. "*A Facile Route to Tripyrrane from 2,5–Bis(hydroxymethyl)pyrrole and the Improved Synthesis of Porphine by the "3+1" Approach,*" Synlett 1, 73–74 (1999).

Hasan et al. "*Synthesis and Reactions of N–Protected 2–Lithiated Pyrroles and Indoles, The tert–Butoxycarbonyl Substituent as a Protecting Group,*" J. Org. Chem. 46, 157–164 (1981).

\* cited by examiner

*Primary Examiner*—Joseph K. McKane
*Assistant Examiner*—Kamal Saeed
(74) *Attorney, Agent, or Firm*—Needle & Rosenberg, P.C.

(57) ABSTRACT

One aspect of the present invention relates to a method of forming chemical compounds and, in particular, chemical intermediates having one or more pyrrole sub-units and at least one protecting group bonded to an atom within a pyrrole sub-unit. The method further involves removal of the protecting group so as to provide a desired chemical compound having one or more pyrrole sub-units. The method can be employed in making porphyrin compounds.

11 Claims, 2 Drawing Sheets

N-PROTECTED SYNTHESIS METHOD FOR USE IN MAKING PORPHYRINS

CROSS REFERENCE TO RELATED APPLICATIONS

This application is related to copending provisional application Ser. No. 60/123,962, filed Mar. 12, 1999, which is incorporated by reference, and claims the benefit of its earlier filing date under 35 USC Section 119(e).

BACKGROUND OF THE INVENTION

The present invention relates to a synthesis method involving the use of protecting groups which method can be useful in making dipyrromethanes (DPM), tripyrrodimethanes (TPM), as well as various bilanes, bilenes, and biladienes. Moreover, the inventive method provides a technique suitable for use in synthesizing. The present invention further relates to a variety of inventive compounds including a number of starting materials and intermediates.

Currently there is no commercial source of dipyrromethane due to its instability and its tedious and dangerous synthesis. The currently preferred procedure requires the use of thiophosgene, which is an extremely toxic and volatile nerve agent. This method can provide dipyrromethane in about a 40% yield in three steps. A more recent procedure discussed in literature can produce dipyrromethane in about 40% yield in one step from simple starting materials, however, the isolation involves a tedious chromatographic procedure requiring a base stabilizing agent. The pure material is not stable at room temperature for any extended periods of time. The initial reaction conditions, the isolation, and the instability of the resulting product do not make this route attractive for commercial scale production.

Attention is also directed towards the following patents and literature references which are incorporated by reference in their entirety for all purposes. U.S. Pat. No. 5,241,062 to Wijesekera et al.; U.S. Pat. No. 5,760,217 to Wijesekera et al.; U.S. Pat. No. 5,767,272 to Wijesekera et al.; U.S. Pat. No. 5,554,764 to Verkade et al.; U.S. Pat. No. 5,672,717 to Verkade et al; U.S. Pat. No. 5,124,449 to Franck et al.; U.S. Pat. No. 5,756,724 to Vogel et al.; JP 1238585 A, assigned to Maruyama K; JP 63238078 A, assigned to Central Glass Co. Ltd.; JP 63238057 A, assigned to Central Glass Co. Ltd.; *J. Am. Chem Soc.*, Abell et al., 120, 1741–1746 (1998); *Tetrahedron Letters*, Wang et al., 37, 3247–3250 (1996); *Tetrahedron Letters*, Kuroda et al., 30, 2411–2412 (1989); *Bull. Chem. Soc. Jpn.*, Kinoshita et al., 65, 2660–2667 (1992); *Chemistry Letters*, Kinoshita et al., 7, 1107–1108 (1989); *Synthesis*, Tietze et al., 851–857 (1996); *J. Porphyrin Phthalocyanines*, Bruckner et al., 2, 455–467 (1998), *BIORG KHIM* Isaeva et al., 5(7) 1146–1150 (1979); *Liebigs Ann. Chem.*, Triebs et al., 718, 183–207 (1968); *J. Porphyrin Phthalocyanines* Lin et al. 2, 363–368 (1998); *Porphyrins and Metalloporphyrins,* Smith, Chap. 2, 29–58 (1979); *Tetrahedron Letters*, Manka et al., 30, 6989–6992 (1989); and *Synlett* 1999, Taniguchi et al., No. 1, 73–74 (1999).

Japanese patent applications JP 63238057 and JP 63238078 to Central Glass Co. Ltd. disclose methods of preparing unsymmetrically 3,4-disubstituted, 2-hydroxymethyl-pyrroles, with at least one perfluoroalkyl substituent. Japanese patent application 1238585 to Murmyama discusses a different method of preparation of unsymmetrical 3,4-disubstituted-2-hydroxymethylpyrroles with a variety of alkyl substituents.

U.S. Pat. No. 5,241,062 to Wijesekera et al. discloses methods of making and using compounds with "leaving group" substituents bonded to the oxygen of 3,4-disubstituted-2-hydroxyalkyl-pyrroles. The leaving groups disclosed included variously substituted benzoates and sulfonates.

Kinoshita et al. (in their 1989 and 1992 articles) disclose methods for the synthesis of substituted pyrroles which contain p-toluenesulfonate groups bonded to the pyrrole nitrogen atoms, and a variety of "leaving groups" on the 2-alkyl substituted pyrroles, including alkoxide, organonitrogen and mono-organo substituted sulfur groups.

Wang et al. disclose a method of reacting N-tosyl-protected 2-formyl-4-aryl-pyrroles, which are useful precursors of porphyrins with beta-aryl substituents.

Abell et al. disclose that various electron withdrawing protecting groups attached to the nitrogen atom of a pyrrole deactivate and stabilize pyrrole rings.

Tietze et al. disclose certain substituted hydroxymethyl pyrrole compounds with N-protecting groups, including tosyl and BOC protecting groups, and certain attempts to couple the substituted and protected hydroxymethylpyrrole compounds with unsubstituted pyrrole compounds.

Vogel et al. disclose the use of BOC groups to protect pyrrole nitrogens during a copper catalyzed coupling reaction of halo-pyrroles, to synthesize bipyrroles, and removal of the BOC groups from the bipyrroles by hydrogenation or thermal treatment.

Smith reviews numerous prior art methods of synthesizing substituted bilane and bilene compounds, including a number of methods that utilize dipyrromethane and tripyrromethane starting materials.

Franck et al. disclosed a synthesis of unusual "azaporphyrin" derivatives containing extra ethylene groups and nitrogen atoms bonded within the main porphyrin ring system.

Isaeva has disclosed a step-wise synthesis of porphyrins involving dipyrromethane, tripyrromethane, and biladiene intermediates which contain various protecting groups (including t-butoxycarbonyl) bonded to the carbon atoms of pyrrole rings.

The need still exists for an improved method for synthesis DPM as well as other compounds containing pyrrole sub-units.

SUMMARY OF THE INVENTION

The present invention is based, at least in part, on the surprising discovery that the use of protecting groups can greatly stabilize a variety of dipyrrolmethanes, tripyrromethanes, bilanes and bilenes. Moreover, these compounds can effectively, economically and rapidly be protected as needed for subsequent use with synthesis of porphyrins. This protection can thus provide for easier purification, isolation, storage and transportation of these compounds.

One aspect of the present invention relates to a method of forming chemical compounds and, in particular, chemical intermediates having one or more pyrrole sub-units and at least one protecting group bonded to an atom. within a pyrrole sub-unit. The method further involves removal of the protecting group so as to provide a desired chemical compound having one or more pyrrole sub-units.

Another aspect of the present invention relates to methods of making the protecting group containing compounds as well as the resulting chemical compounds and/or intermediates.

Yet another aspect of the invention relates to pyrrole intermediates and, in particular, sulfonium salt intermediates used in forming the protecting group-containing pyrrole compounds.

In particular, the present invention includes, but is not limited to, the following synthesis techniques for forming protective group containing compounds:

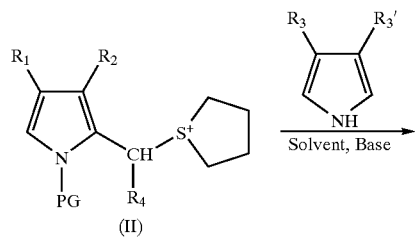

(II)

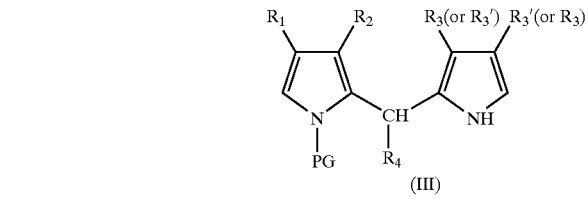

(III)

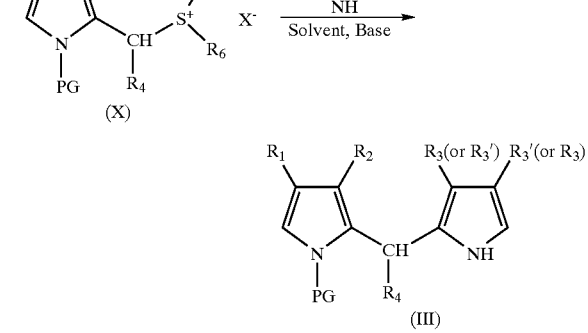

(X)

(III)

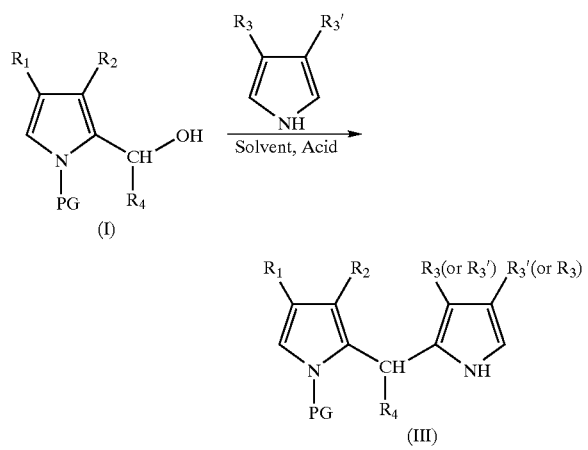

(I)

(III)

where $R_1$, $R_2$, $R_3$, $R_3'$, $R_4$, $R_5$, and $R_6$ include carbon atom-containing substituents including hydrogen, and hydrocarbon groups such as alkyl, aryl, alkenyl, alkynyl groups, which groups can optionally include substituents and heteroatoms in connection therewith, as well as a deprotection scheme such as that illustrated in connection with DPM:

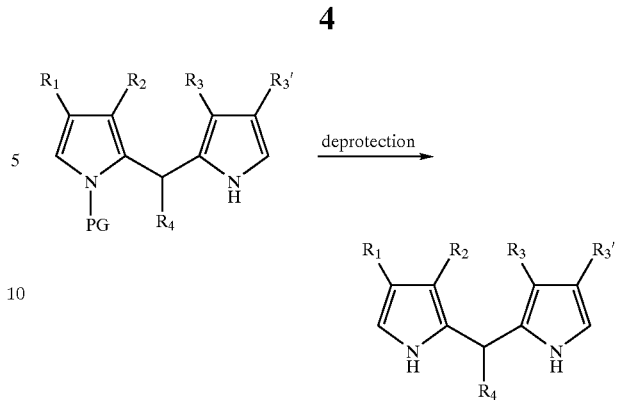

where the protecting group, PG, is discussed in more detail below.

Moreover, the invention relates to a number of starting materials and intermediates including:

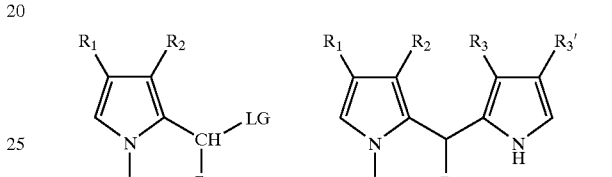

(VI)

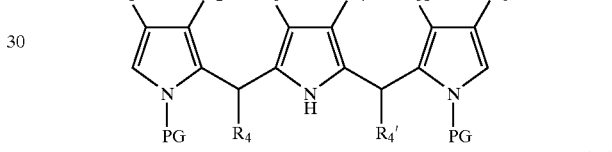

(IV)

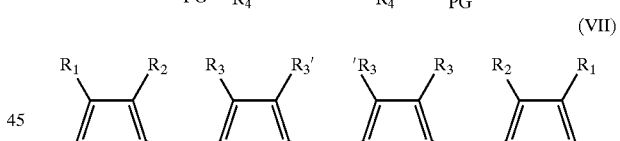

(VII)

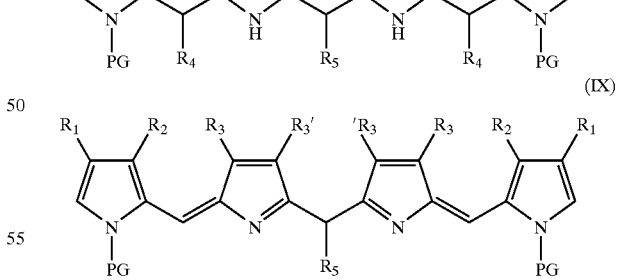

(IX)

DETAILED DESCRIPTION OF THE PREFERRED EMBODIMENTS

Figure 1:
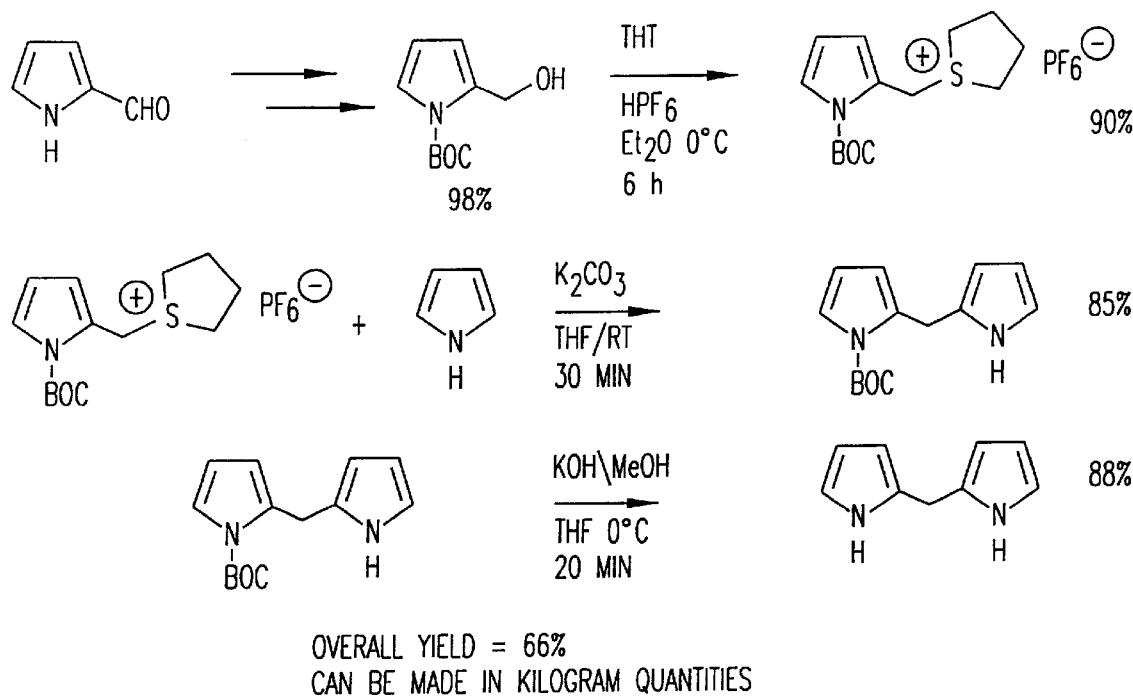
FIGS. 1 and 2 illustrate two examples of the inventive process.
Figure 1:
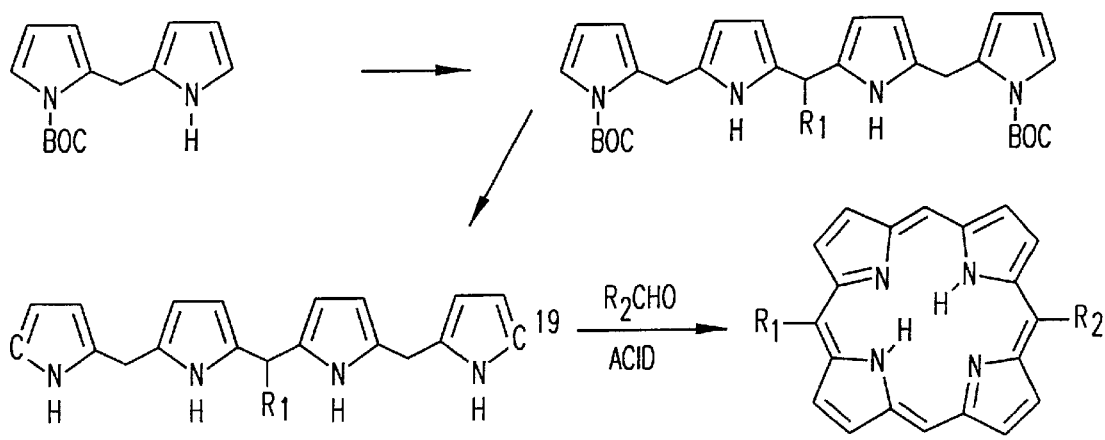

As discussed above, the present invention involves to the use of protecting groups that are bonded to an atom within a pyrrole compound. These pyrrole compounds can be employed in forming various chemical compounds and, in particular, chemical intermediates having one or more pyrrole sub-units. The protecting group can then be removed as illustrated below in connection with DPM.

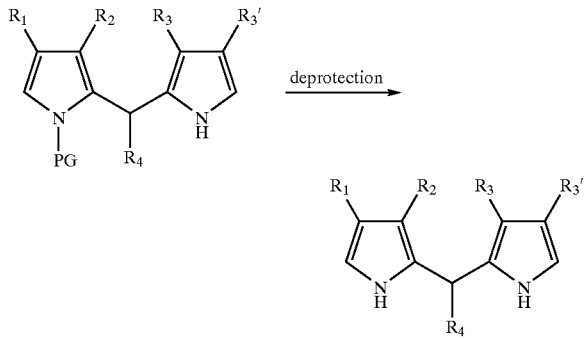

While DPM is illustrated, this embodiment of the invention can also be employed in the synthesis of protected chemical intermediates having three or more pyrrole sub-units such as TPM, bilane, bilenes and biladienes.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims that follow, reference will be made to a number of terms that shall be defined to have the following meanings:

"Optional" or "optionally" means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted lower alkyl groups and lower alkyl groups where there is substitution.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain from 1 to 12 carbon atoms. The term "lower alkyl" intends an alkyl group of from one to six carbon atoms, preferably from one to four carbon atoms. The term "cycloalkyl" intends a cyclic alkyl group of from three to eight, preferably five or six carbon atoms.

Similarly, the term "alkenyl" as used herein refers to an unsaturated aliphatic branched or unbranched hydrocarbon chain containing from 1 to 24 carbon atoms, and having a double bond between carbon atoms while "alkenyl" refers to similar groups having a triple bond between carbon atoms.

The term "aryl" as used herein describes substituted or unsubstituted benzene-like compounds of six to twenty five carbon atoms having at least one 6-membered ring residue of carbon atoms, with alternating (conjugated) double bonds which have 4n+2 Π electrons, wherein n is a positive integer.

The mono-pyrrole compounds which can be employed in forming the chemical intermediates include those illustrated below.

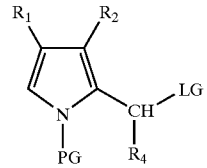

where LG is a leaving group such as —OR, —SR, —NR$_2$, and the like, with R preferably being hydrogen, alkyl, aryl, alkenyl, or alkynl group, and PG is a protecting group.

Protecting groups, per se, are recognized in the art as a substituent group selected to direct the "chemistry" of the molecule away from the group being protected. A preferred protecting group for the purposes of this invention is a substituent which can be easily bonded to an atom, preferably the nitrogen atom, of a pyrrole ring. Thus, in a particularly preferred embodiment of the invention, the group is a replacement for a nitrogen hydrogen atom. The protecting group can later be easily and selectively removed by physical or chemical treatment, e.g., to liberate and regenerate a pyrrolic bond, preferably a pyrrolic nitrogen-hydrogen bond.

The protecting groups useful in this invention are typically electron withdrawing groups and/or groups that "deactivate" the chemical reactivity of the pyrrole intermediates, or modify the relative reactivity of various positions on the pyrrole rings.

Preferred protecting groups for use in the present invention include those recognized in the art for use in connection with pyrrole compounds. See, for example, "Protective Groups In Organic Synthesis" 2$^{nd}$ Ed., T. Greene and P. Wuts, Wiley Interscience, 1991, and, in particular, pp. 381–397, which are incorporated by reference.

Specific examples of preferred protecting groups include t-butoxycarbonyl (BOC), methanesulfonate (MES), toluenesulfonate (TOS), allyl and allyloxycarbonyl groups.

According to the present invention, protecting groups enable the synthesis of compounds via step-wise reaction sequences that would not be feasible without the protecting groups. The protecting groups often improve chemical yields, and improve the solubility of the compounds, so that larger absolute quantities of products can be produced and purified more efficiently and economically. The protecting groups can also stabilize pyrrole compounds (which can often be unstable) during handling, storage, and shipping, then be readily removed just prior to use of the intermediate, thus providing a significant commercial advantage.

The term "leaving groups" is recognized in the art and, as such, suitable leaving groups include those leaving groups which are known in the art with positively charged, trialkylsulfur atoms being preferred. These leaving groups can be introduced onto any suitable atom in the pyrrole compound which atom would allow said groups to be readily displaced during, e.g., condensation of the pyrrole compound with another pyrrole compound. Preferred location(s)

for the leaving group(s) include the α-position of alkyl substituents at the 2 or 5 positions of the pyrrole ring.

Suitable classes of pyrrole compound are N-protected pyrrole compounds having sulfonium salt leaving groups which are illustrated below.

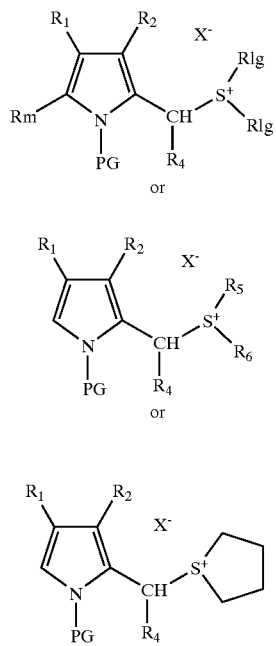

with $R_m$ being defined as $R_1$–$R_6$ above. $R_4$ is preferably hydrogen.

Preferred Rm groups include hydrogen and/or methyl ($CH_3$) groups, particularly in embodiments involving the preparation of porphyrin compounds.

Class (II), (X), and (XI) pyrrole compounds can be prepared by treating N-protected precursor pyrroles, such as (I), with diorgano-substituted sulfur compounds, to give novel pyrrole compounds with sulfonium "leaving groups".

The sulfonium "leaving groups" are readily displaced when compound (II), (X), or (XI) is condensed with another pyrrole compound (shown with $R_3$ or $R_3'$ substituents), under basic conditions. For example:

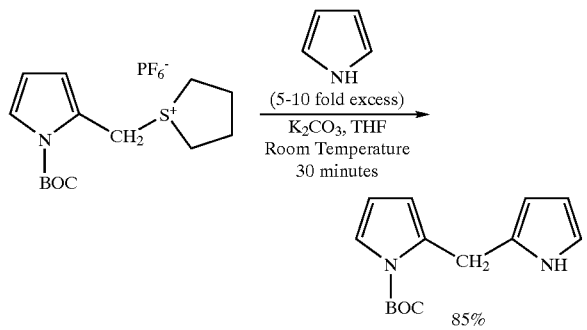

The N-BOC dipyrromethanes can then be reacted to remove the protecting group:

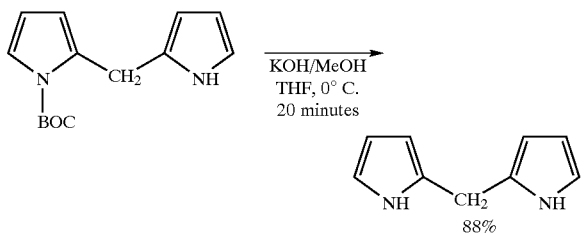

Although the sulfonium group comprising the five-membered ring shown above may be a preferred embodiment, it is clear that other sulfur substituents can be employed. These substituents include carbon-containing substituents recognized in the art such as alkyl, aryl, alkenyl, alkynl and the like.

Other examples of suitable pyrrole compounds include those pyrrole compounds represented by the following formula.

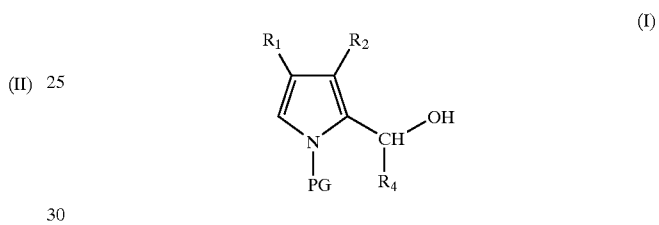

Applicant's have unexpectedly discovered that compounds of class (I) can be condensed with other pyrroles, in the presence of acid, to give good yields (greater than about 25% and up to about 50–70% or more) of N-protected dipyrromethanes. In particular, Applicant's have discovered that condensation of 1-tert-butoxycarbonyl)-2-hydroxymethyl pyrrole with an excess, preferably a five to tenfold excesses, of another pyrrole (such as pyrrole itself) can produce good yields of the N-protected dipyrromethanes which are desired for the synthesis of porphyrins, according to the methods of the invention.

A preferred process according to the present invention includes the following steps:

(1) reacting one or more pyrrole compounds together so as to provide a protected intermediate compound having two or more pyrrole sub-units, and at least one N-protecting group.

(2) deprotecting of the chemical intermediate by removing one or more of the N-protecting group(s).

The first step of this process involves reacting the pyrrole starting materials together so as to provide a chemical intermediate containing one or more pyrrole sub-units. In this regard, it is preferred to react the pyrrole compounds together so as to provide an intermediate containing 2 to 4 pyrrole sub-units. A method for reacting pyrrole compounds can involve, e.g., a condensation reaction.

A second step of the method involves "deprotection" of the protecting group-containing compounds so as to provide the desired unprotected compound. The method of deprotection can involve physical, e.g., thermal, or chemical treatment of the compound. For example, an N-protecting group such as BOC on DPM can be removed under basic conditions and the crude dipyrromethane requires only a charcol treatment to provide an excellent yield of pure white crystalline dipyrromethane.

Other techniques for "deprotection" include those discussed in connection with the protecting groups disclosed in the *Journal of Organic Chemistry*, Hasan et al., 46, 157–164 (1981) which is incorporated by reference, as well as the Greene and Wuts text discussed above.

The deprotection technique of the present invention is capable of providing significant commercial advantages because unprotected dipyrromethanes are often unstable to light, oxygen, or even acids, while the N-protected materials have a much greater stability. Thus, the ultimate commercial sale and shipment of protected materials followed by deprotection prior to use could provide a significant technical and commercial advantage.

The protection reaction methods according to the present invention further allows for the "step-wise" synthesis of bilanes and porphyrins of known regiochemical substitution. In particular, the easy synthesis of bilanes unsubstituted at the terminal carbons is possible by acid catalyzed condensation of dipyrromethane with various aldehydes.

Specific examples of processes using mono-pyrrole compounds according to the present invention to produce a variety of DPM, TPM, bilanes, bilenes, and biladienes are illustrated by the following Schemes 1–3.

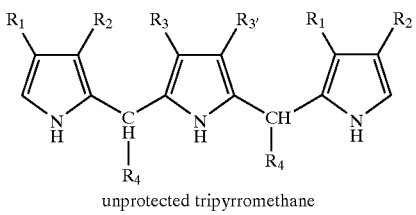
unprotected tripyrromethane

Scheme 1b

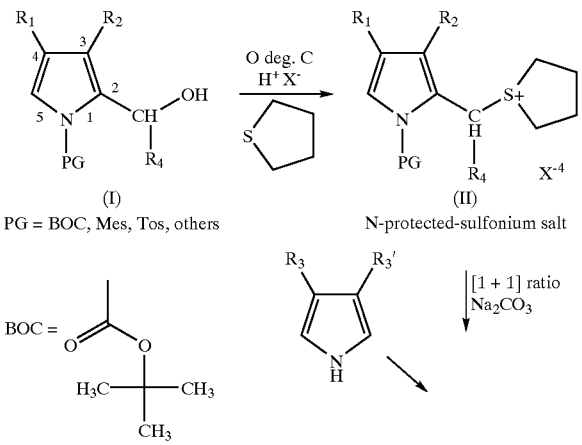

Scheme 1a

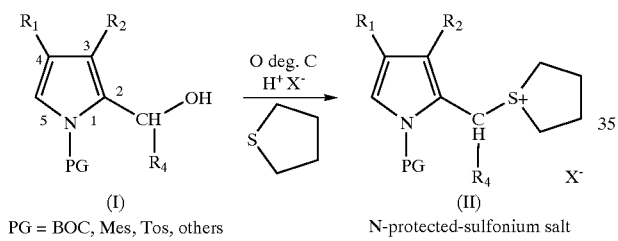

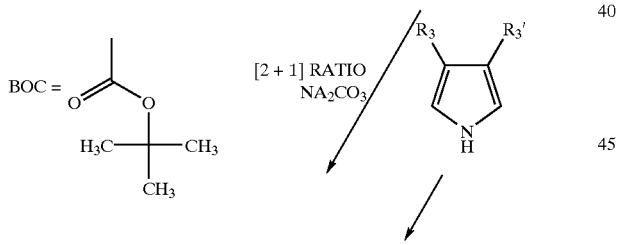

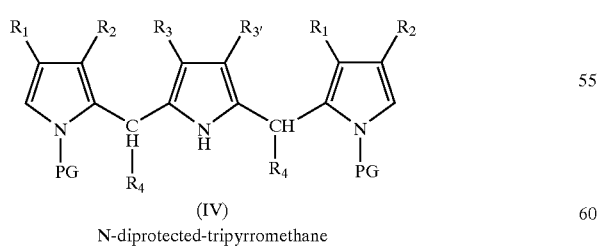
(IV)
N-diprotected-tripyrromethane

|deprotect

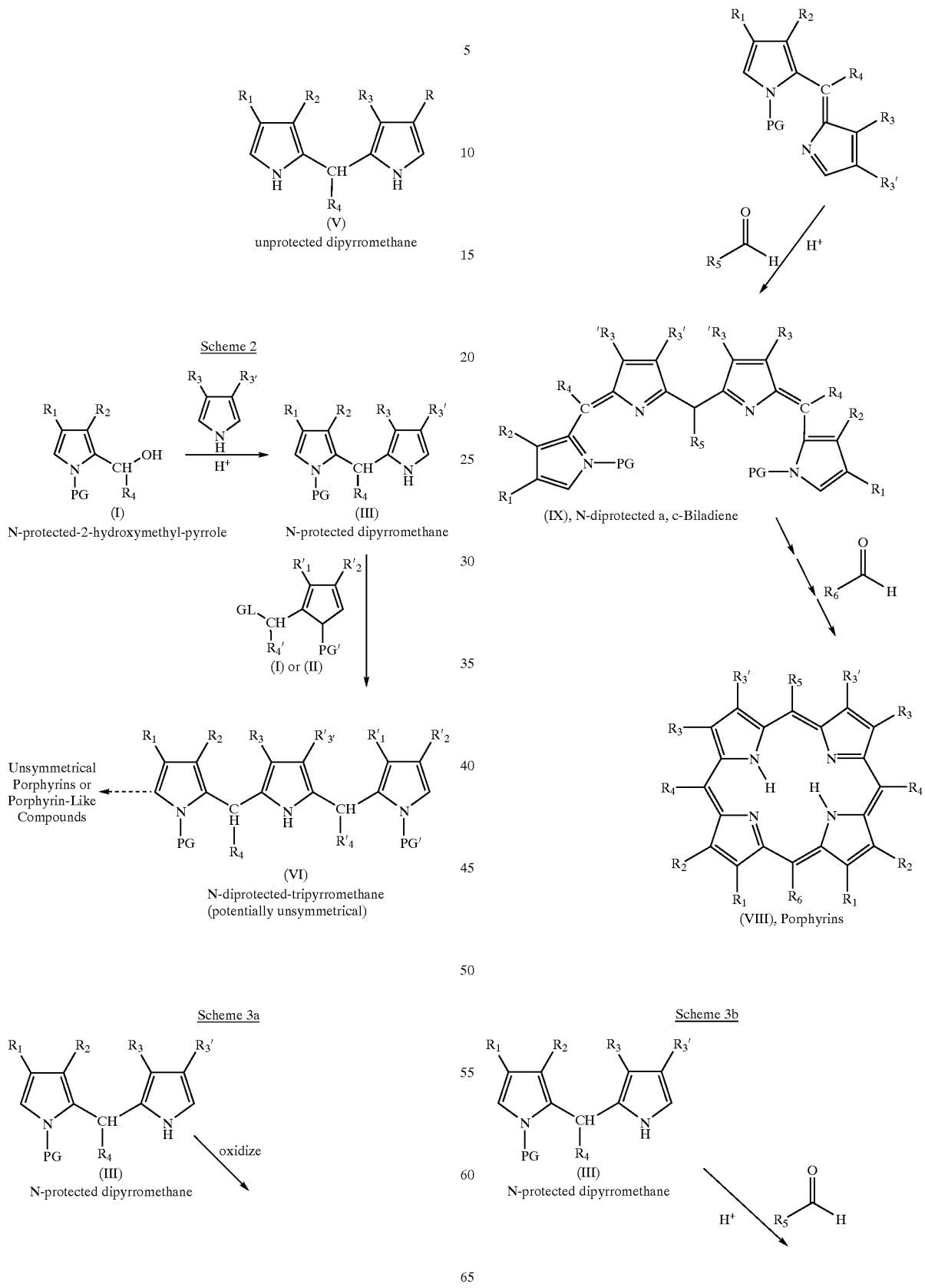

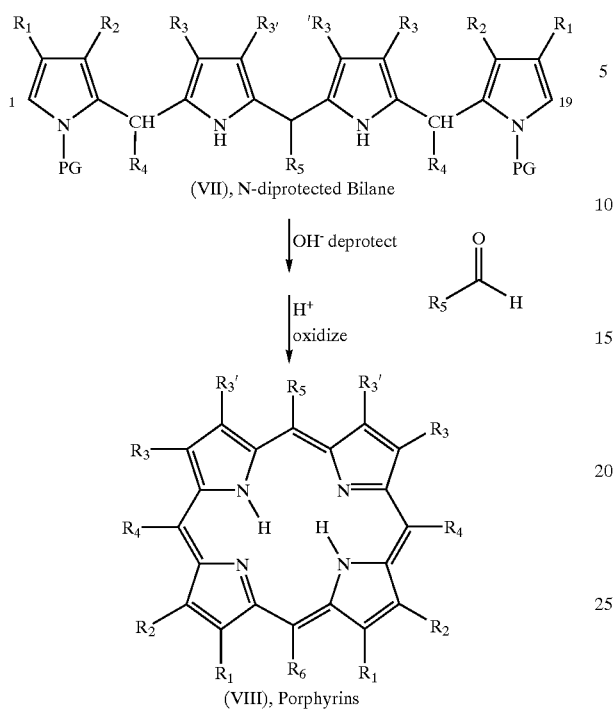

(VII), N-diprotected Bilane

↓ OH⁻ deprotect

↓ H⁺ oxidize $R_5$—CHO (VIII), Porphyrins

As can be seen from schemes 3a and 3b, the various chemical intermediates associated with the claimed invention can be employed in the synthesis of porphyrin or metallo-porphyrins. In this regard, the pyrrole sub-unit containing compounds can be deprotected and then reacted under conditions which are known in connection with the conversion of DPM to porphyrins. For example, the TPM reaction can be performed with the presence of an alkehyde under conditions primarily used in connection with DPM.

One of the reaction conditions involves selection of a preferred solvent depending on the particular protecting group employed. For example, when BOC is used, the preferred solvent is a mixture of THF and MeOH.

There is currently a tremendous amount of scientific, technological, and biomedical interest in a wide variety of "porphyrin-like" materials. See, for example, U.S. Pat. No. 5,124,449 to Franck, et al.

The convergent nature of the resulting methodology allowed by this invention leads to a modular or building block approach to porphyrins. To this end, the compounds of the present invention can be used as "building block" molecules in the synthesis of potentially wide varieties of "porphyrin-like" materials. This means that a variety of porphyrins suitable for use in a wide range of environments could be synthesized from a few starting materials through a mix and match approach.

Another advantage of this step-wise porphyrin methodology lies in the higher throughput to final products. For example, trans-diphenylporphyrin can be made in ca. 60–65% yield from dipyrromethane and benzaldehyde at 0.0025M. Using the step-wise approach, diphenylporphyrin can be made in 60–65% yield at 0.01M. This means that four times the amount of material can be produced in the same size reaction vessel.

The present invention also relates to those compounds having the following formula which are not disclosed in the prior art:

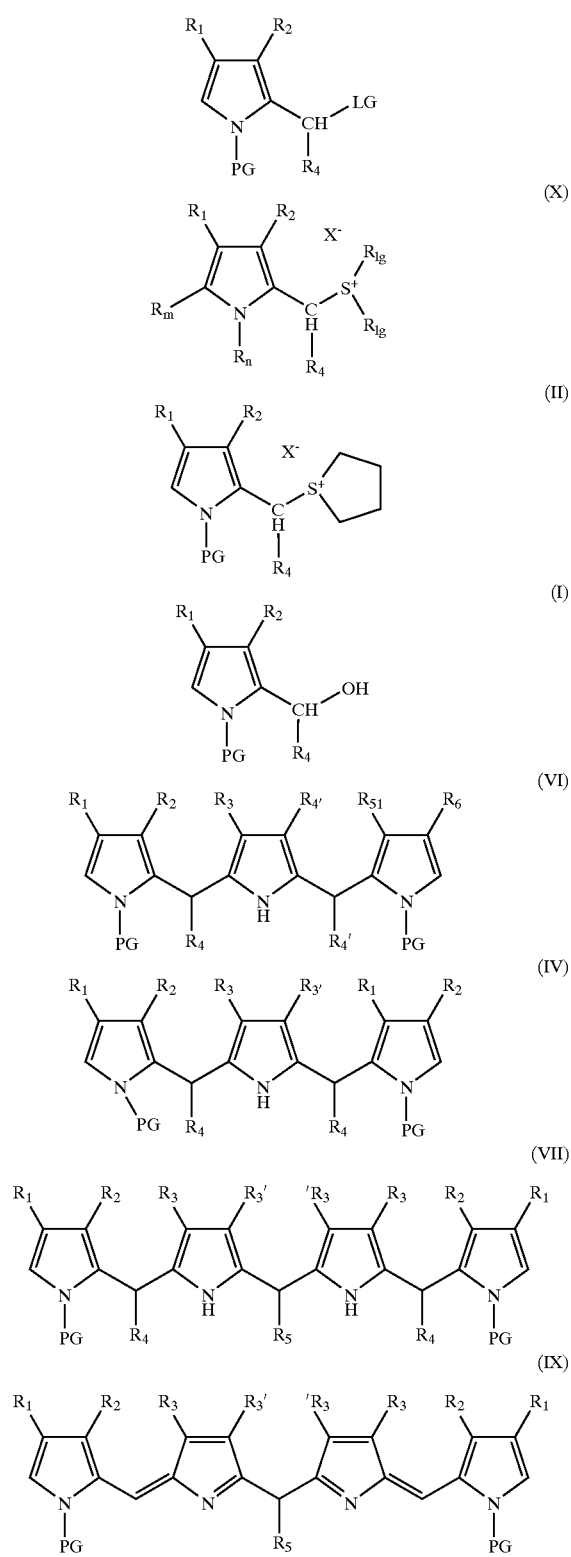

where the substituents are defined previously.

The herein described "protected" compounds such as dipyrromethane can be stable at room temperature, can require only a trivial chromatographic procedure without any stabilizers, can circumvent the need for thiophosgene, and can be easily made in commercial quantities. The enhanced stability allows for easy long-term storage, shipping and handling. An advantageous feature in this methodology is that the condensation reaction can be performed under mild basic conditions, to which pyrrole compounds are more stable, rather than the traditional acid-catalyzed condensation. In comparison to the more traditional techniques, the overall yield from the same starting material (pyrrole) for this protection-deprotection methodology can be 10–15% higher.

EXAMPLE

Figure 2:
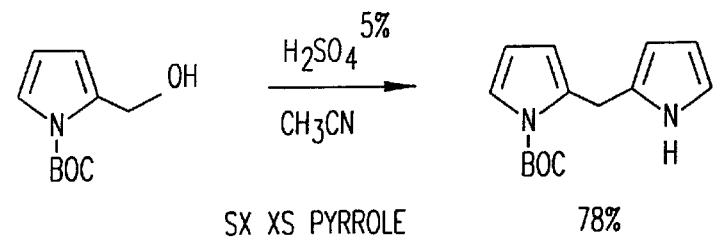
Figure 2:
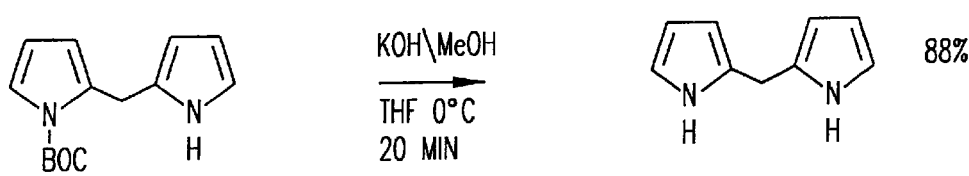
Figure 2:
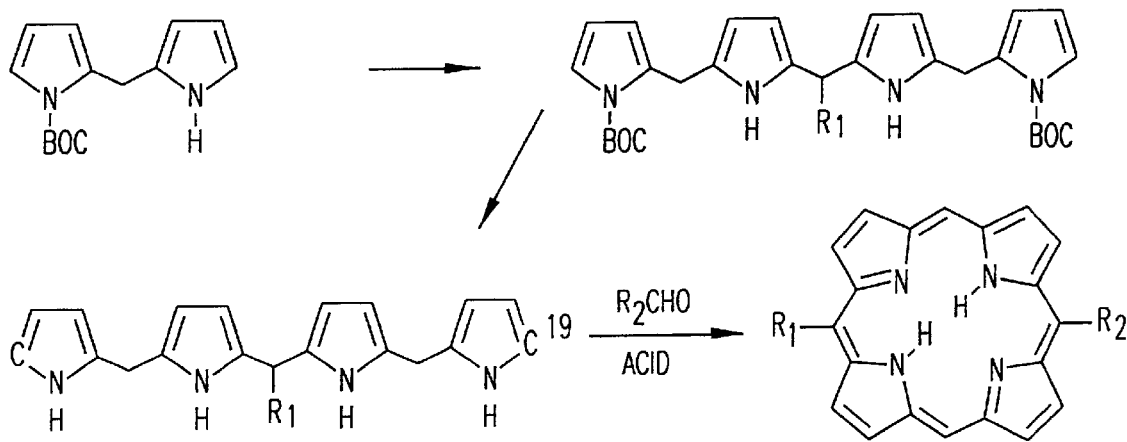

Two specific examples of a method according to one aspect of this invention is illustrated by the sequence of steps in FIGS. 1 and 2 respectively.

This invention may be embodied in many different forms and should not be construed as limited to the embodiments set forth herein; rather, these embodiments are provided so that this disclosure will be thorough and complete, and will fully convey the scope of the invention to those skilled in the art.

For example, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for preparing pyrromethene compound having at least two pyrrole sub-units, comprising:
    a. reacting one or more N-protected pyrrole compounds with a pyrrole compound so as to provide a chemical intermediate having at least two pyrrole sub-units, and at least one N-protecting group bonded to the nitrogen atom of one of the pyrrole sub-units; and
    b. deprotecting the chemical intermediate by removing one or more of the protecting groups from the chemical intermediate.

2. The method according to claim 1, wherein the chemical intermediate has two pyrrole sub-units.

3. The method according to claim 1 wherein the chemical intermediate has three pyrrole sub-units.

4. The method according to claim 3 wherein the chemical intermediate is a compound of formula:

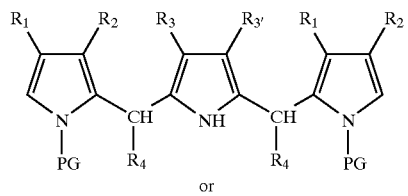

or

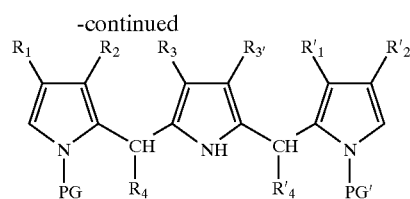

where $R_1$, $R_2$, $R_3$, $R_3'$, $R_4$ and $R_4'$ are hydrogen or carbon-containing substituents and PG and PG' are protecting groups.

5. The method according to claim 1, wherein step (a) comprises condensation of the pyrrole compounds.

6. The method according to claim 1, wherein the N-protecting group is BOC, MES, or TOS.

7. The method according to claim 1, wherein the N-protected pyrrole compound is a compound of the formula:

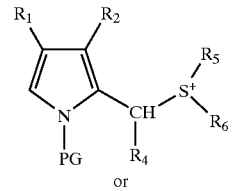

or

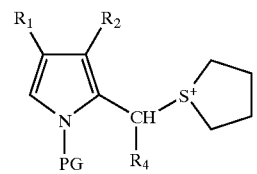

where $R_1$, $R_2$, $R_4$, $R_5$ and $R_6$ are hydrogen or carbon-containing substituents and PG is a protecting group.

8. The method according to claim 1 wherein the chemical intermediate is a compound of the formula

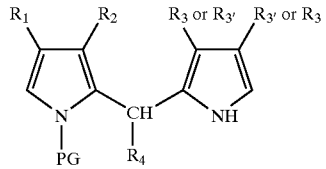

where $R_1$, $R_2$, $R_3$, $R_3'$ and $R_4$ are hydrogen or carbon-containing substituents and PG is a protecting group.

9. The method of claim 1, wherein the chemical intermediate is a dipyrromethane.

10. The method of claim 1, wherein the chemical intermediate is a tripyrromethane.

11. The method of claim 1, wherein the chemical intermediate is a bilane, bilene, or biladiene.

* * * * *

UNITED STATES PATENT AND TRADEMARK OFFICE
CERTIFICATE OF CORRECTION

PATENT NO. : 6,528,659 B1
DATED : March 4, 2003
INVENTOR(S) : Nickel et al.

It is certified that error appears in the above-identified patent and that said Letters Patent is hereby corrected as shown below:

Column 15,
Line 33, after "A method for preparing" and before "pyrromethane compound" insert: -- a --.
Lines 49-55, delete in figure $R_{3'}$" and insert: -- $R_3$' --.

Column 16,
Lines 1-8, delete in figure "$R_{3'}$" and insert: -- $R_3$' --.
Lines 41-48, delete in the figure "$R_{3'}$" and insert: -- $R_3$' --.

Signed and Sealed this

Seventeenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,528,659 B1
DATED : March 4, 2003
INVENTOR(S) : Ni et al.

It is certified that error appears in the above-identified patent and that said Letters Patent is hereby corrected as shown below:

Column 1,
Line 4, please insert the following before "Cross References to Related Applications:"

-- ACKNOWLEDGMENTS
This invention was made with government support under Grant CA40157 awarded by National Institutes of Health. The government has certain rights in the invention. --

Signed and Sealed this

Twenty-eighth Day of June, 2005

JON W. DUDAS
*Director of the United States Patent and Trademark Office*